(12) United States Patent
Helmer et al.

(10) Patent No.: US 8,986,259 B2
(45) Date of Patent: *Mar. 24, 2015

(54) PISTON ROD ASSEMBLY FOR A DRUG DELIVERY DEVICE

(75) Inventors: Michael Helmer, Frankfurt am Main (DE); Christoph Eissengarthen, Dexheim (DE); Winfried Huthmacher, Hattersheim (DE); Carsten Mosebach, Mainz (DE); Leo Zeimetz, Büttelborn (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1151 days.

This patent is subject to a terminal disclaimer.

(21) Appl. No.: 12/791,499

(22) Filed: Jun. 1, 2010

(65) Prior Publication Data

US 2011/0245780 A1 Oct. 6, 2011

(30) Foreign Application Priority Data

Mar. 31, 2010 (EP) .................................. 10158613

(51) Int. Cl.
*A61M 5/315* (2006.01)
*A61M 5/24* (2006.01)
*A61M 5/31* (2006.01)

(52) U.S. Cl.
CPC .............. *A61M 5/31515* (2013.01); *A61M 5/24* (2013.01); *A61M 5/3146* (2013.01); *A61M 5/31511* (2013.01); *A61M 5/31555* (2013.01); *A61M 5/3156* (2013.01); *A61M 5/3158* (2013.01); *A61M 2005/2407* (2013.01); *A61M 2005/3152* (2013.01); *A61M 2207/00* (2013.01)
USPC ............ 604/209; 604/224; 604/228; 604/232

(58) Field of Classification Search
CPC ... A61M 5/24; A61M 5/3146; A61M 5/3156; A61M 5/3158; A61M 5/31511; A61M 5/31515; A61M 5/32155; A61M 2005/2407; A61M 2005/3152; A61M 2207/00
USPC ............ 604/136, 187, 68, 70, 207–211, 218, 604/220, 224, 225, 228, 229, 232–235
See application file for complete search history.

(56) References Cited

U.S. PATENT DOCUMENTS 3,224,445 A * 12/1965 Melott .......................... 604/228
4,064,879 A * 12/1977 Leibinsohn ................... 604/121
4,333,458 A * 6/1982 Margulies et al. ............ 604/220

(Continued)

FOREIGN PATENT DOCUMENTS

WO WO 2009095332 A1 * 8/2009

*Primary Examiner* — Nathan R Price
(74) *Attorney, Agent, or Firm* — McDonnell Boehnen Hulbert & Berghoff LLP

(57) ABSTRACT

Various embodiments of piston rod assemblies, drug delivery devices making use of such piston rod assemblies, and methods for assembling such piston rod assemblies and drug delivery devices are provided. In one embodiment, a piston rod assembly for a drug delivery device is provided, wherein the piston rod assembly is configured to engage a piston of a medicament cartridge. The piston rod assembly comprises (i) a piston rod, (ii) at least one adjusting member displaceably engaged with a distal end section of the piston rod, wherein the at least one adjusting member is displaceable along a long axis of the piston rod, and (iii) at least one interlock member configured to mutually lock the at least one adjusting member and the piston rod in an arbitrary relative axial position.

17 Claims, 3 Drawing Sheets

(56) References Cited

U.S. PATENT DOCUMENTS

| | | | | |
|---|---|---|---|---|
| 4,492,576 | A | * | 1/1985 | Dragan .......................... 433/90 |
| 5,730,729 | A | * | 3/1998 | Bergstresser et al. ......... 604/228 |
| 5,743,889 | A | * | 4/1998 | Sams ........................... 604/211 |
| 5,921,966 | A | * | 7/1999 | Bendek et al. ................ 604/207 |
| 7,678,084 | B2 | * | 3/2010 | Judson et al. ................. 604/187 |
| 8,475,414 | B2 | * | 7/2013 | Boyd et al. ................... 604/218 |
| 2006/0129122 | A1 | * | 6/2006 | Wyrick ......................... 604/506 |
| 2006/0270985 | A1 | * | 11/2006 | Hommann et al. ........... 604/136 |
| 2011/0046567 | A1 | * | 2/2011 | Radmer et al. ................ 604/218 |
| 2012/0041386 | A1 | * | 2/2012 | Veasey et al. ................ 604/211 |
| 2012/0095413 | A1 | * | 4/2012 | Nzike et al. .................. 604/211 |
| 2012/0172804 | A1 | * | 7/2012 | Plumptre ..................... 604/154 |
| 2012/0289908 | A1 | * | 11/2012 | Kouyoumjian et al. ...... 604/211 |
| 2012/0310206 | A1 | * | 12/2012 | Kouyoumjian et al. ...... 604/506 |
| 2014/0236096 | A1 | * | 8/2014 | Helmer et al. ................ 604/208 |

* cited by examiner

PISTON ROD ASSEMBLY FOR A DRUG DELIVERY DEVICE

CROSS-REFERENCE TO RELATED APPLICATIONS

This application claims the benefit of European Patent Application No. 10158613.9, filed on Mar. 31, 2010, the contents of which are incorporated herein by reference.

BACKGROUND a. Field of the Invention

The present invention relates to a piston rod assembly for a drug delivery device that allows a user to select single or multiple doses of an injectable medicinal product and to dispense and deliver the set dose to a patient. In particular, the present invention relates to such drug delivery devices that are handled by the patients themselves, such as pen-type injectors.

b. Description of the Related Art

Drug delivery devices for administering single or multiple doses of an injectable medicinal product are well-known in the art. Generally, such devices have substantially the same purpose as that of an ordinary syringe.

Drug delivery devices of this kind have to meet a number of user specific requirements. For instance, in the case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Typically, the medicinal product to be administered is provided in a cartridge that has a moveable piston (also commonly referred to as a "bung", a "stopper", or a "plunger") mechanically interacting with a piston rod of a drive mechanism of the drug delivery device. By applying thrust to the piston in the distal direction, a certain amount of the medicinal fluid is expelled from the cartridge and may be administered to the patient by some kind of needle assembly being in fluid communication with the cartridge.

Due to inevitable manufacturing tolerances of the device and the cartridge there may for instance persist axial clearance between a cartridge's piston and the piston rod when the device is finally assembled. Typically, prior to a primary use of the device, an end-user, e.g. a patient has to conduct a so-called set-up or priming of the drive mechanism in order to ensure, that the piston of the cartridge and the piston rod are located at a pre-defined position with respect to each other, thus ensuring, that with an initial dose setting and a subsequent dose dispensing step, a predefined amount of the medicinal product can be disposed in an accurate way. By way of the set-up step, mechanical tolerances of movable components of the drug delivery device can be significantly reduced or eliminated.

Drug delivery devices are assembled in a mass production process in which for instance two housing components of the drug delivery device receive a cartridge and a drive mechanism including the piston rod, respectively. Then, in a final step of assembly, the two pre-configured housing components or respective sub-assemblies are mutually interconnected. When reaching a defined final assembly configuration, it would be beneficial for the piston rod and the piston of the cartridge to either mutually abut or to be separated by a pre-defined gap.

Exact and precise mutual positioning and alignment of the piston and the piston rod is important and crucial for accurate and reliable functionality of the drug delivery device. Moreover, the piston rod should not exert pressure to the plunger during assembly of the drug delivery device or in its final assembly configuration. Otherwise a rather uncontrolled expelling of the medicament prior to a first use of the drug delivery device may result when a needle is attached.

Since at least some or even major components of the drug delivery device are designed as plastic injection molded components, the components themselves, and their assembly are inevitably subject to certain geometric tolerances. Moreover, the cartridge itself and in particular the position of the piston within the cartridge may vary.

SUMMARY

Disclosed herein are various embodiments of piston rod assemblies, as well as various embodiments of dug delivery devices making use of such piston rod assemblies. In addition, various embodiments of methods for assembling such piston rod assemblies and drug delivery devices are described.

In a first aspect, a piston rod assembly is provided for a drug delivery device which is adapted to become operably engaged with a piston of a cartridge that is filled with an injectable fluid, in particular with a medicament, such as insulin. The piston rod assembly is intended to become operably engaged with a drive mechanism of a drug delivery device allowing for setting a pre-defined dose and to induce an axial displacement of the piston rod in the distal direction in order to move the piston of the cartridge in the distal direction for expelling a pre-defined amount of the medicament.

In another aspect, the piston rod may be adapted to be operably engaged with a piston of a cartridge containing a medicament, wherein mutual engagement of the piston rod and the piston may comprise a unidirectional thrust transferring engagement of the piston rod and the piston, e.g., through a mutual and releasable abutment. Hence, the piston rod assembly is adapted and intended to move the piston in only one direction. It is therefore sufficient that the respective abutment surfaces of piston rod assembly and piston are of substantially planar geometry. However, the respective surfaces need not be substantially planer. During a typical dispensing procedure, the cartridge itself is in fluid communication with a piercing assembly, such like a needle, a cannula, an infusion tube or with similar delivery devices.

In another aspect, the cartridge itself may comprise a vial or carpule, and may be sealed at its proximate end by a movable piston. Alternatively, the cartridge may comprise a syringe. Regardless of whether the cartridge comprises a vial, carpule, or a syringe, the cartridge may be adapted and designed for a single use.

In another aspect, the piston rod assembly further comprises at least one adjusting member displaceably disposed at the piston rod. More specifically, the adjusting member may be connected to the piston rod and displaceable with respect to the piston rod, along the piston rod's long axis, hence in axial direction. The adjusting member may be interconnected with a distal end section of the piston rod. Consequently, the at least one adjusting member may be arranged between the piston rod and the cartridge's piston. The adjusting member may therefore serve as a kind of interface member intended to reduce and/or to eliminate variations in the distance between and/or relative positions of the piston rod and the piston. Such variations may be due to manufacturing and/or assembly tolerances.

In another aspect, the piston rod assembly further comprises at least one interlock means which is adapted to interact with the adjusting member and/or with the piston rod for mutually locking in position the adjusting member and the piston rod in an arbitrary relative position to each other. In particular, the adjusting member's axial position relative to the piston rod can be continuously modified for eliminating said manufacturing and assembly tolerances. Once the adjusting member has been positioned in a tolerance-eliminating configuration with the piston rod, its relative position to the piston rod can be either permanently or releasably locked by way of the at least one interlock means.

In accordance with this aspect, during a tolerance eliminating procedure, the adjusting member and the piston rod are mutually displaceable with respect to each other. In other words, they may be telescopically shiftable in axial direction. Once a tolerance-eliminating configuration has been attained, adjusting member and piston rod can be mutually interlocked in such a way, that the piston rod assembly is enabled to transfer a respective thrust to the piston required for displacing the piston in the distal direction. By having a piston rod and an adjusting member displaceably attached or connected, the overall axial dimension and extension of the piston rod assembly becomes variable, in particular for the purpose of tolerance elimination.

In another aspect, the adjusting member and the piston rod may be threadedly engaged in order to axially displace the piston rod and the adjusting member relative to each other. By way of a threaded engagement of adjusting member and piston rod, the overall axial dimensions of the piston rod assembly can be modified in a continuous way. The interlock means may be further adapted to inhibit self-acting relative rotation of the piston rod and the adjusting member. Hence, the interlock means can prevent the adjusting member from autonomously rotating with respect to the piston rod and vice versa. By way of the threaded engagement, axially directed forces and thrust can be transferred, e.g., from a drive mechanism via the piston rod to the adjusting member and finally to the piston of the cartridge. In such an arrangement, the interlock means itself may not need to withstand the comparatively large axial forces or respective thrust, which is required to displace the piston of the cartridge in distal direction.

In a further aspect, the adjusting member comprises a threaded receptacle, which is adapted to receive a correspondingly threaded distal socket portion of the piston rod. In other aspects, the piston rod comprises a threaded receptacle at its distal end section, which is adapted to receive a correspondingly threaded proximal socket portion of the adjusting member. Hence, the threaded engagement of the piston rod and the adjusting member can be generally implemented either way.

In another aspect, the interlock means comprises at least one resiliently biased tongue member which is adapted to engage with a corrugated surface portion or section of the adjusting member or of the piston rod. Herein, a portion or section of a surface of may comprise the entire surface. The interlock means may positively engage with a side wall of the receptacle of either the adjusting member or the piston rod. Additionally, the interlock means may be arranged on that part or component of the piston rod assembly comprising the socket portion.

In another aspect, the tongue member is arranged with a lateral or radial offset with respect to the socket portion. With respect to a transverse plane of the piston rod assembly, i.e., a plane perpendicular to the piston rod's long axis, the axially protruding socket portion is typically arranged in the centre of the piston or on the centre of the adjusting member. Hence, mutual arrangement of the socket portion and the tongue member is such that a gap is formed there between adapted to receive a side wall section of the receptacle.

In a further aspect, the radially inwardly facing side wall section of the receptacle is threaded in order to provide threaded engagement with the correspondingly threaded socket portion. The side wall section of the receptacle at its outwardly facing side may be corrugated or comprise a ribbed structure, by way of which a kind of positive or frictional engagement of the receptacle and the tongue member can be established in order to inhibit self-acting relative rotation of the receptacle relative to the socket portion.

Alternatively it is also conceivable, that an outwardly facing side wall section of the receptacle is threaded and wherein an inwardly facing side wall section of said receptacle is corrugated or comprises a ribbed surface structure. In such configurations, the resiliently biased tongue members may be arranged radially inward with respect to the threaded engagement of the adjusting member and the piston rod.

Mutual engagement and interaction of the resiliently biased tongue members and the corrugated surface provides a kind of snap-in feature. Depending on the overall number of longitudinally extending ribs or corrugations and the pitch of the thread a fine adjustment of the piston rod and the adjusting member can be attained, e.g., in a sub-millimeters range around $1/10$ mm or even $1/100$ mm.

In a further aspect, the threaded and corrugated or ribbed side wall sections of the receptacle are arranged at least partially offset with respect to each other in axial direction. Moreover, the corrugations or the ribs of said wall section comprise an axial extension substantially corresponding with an overall axial extension of the mutually corresponding threads of the receptacle and the socket portion.

According to a further aspect, the piston rod comprises at least two tongue members arranged at a distal end section of the piston rod and axially extending in the distal direction. The tongue members may be arranged opposite to each other in the transverse plane and may comprise radially inwardly pointing lug portions that are adapted to engage with the corrugated or ribbed outer side wall section of a proximal end of the adjusting member comprising a cupped receptacle.

In a further aspect, the adjusting member comprises a contact surface at its distal end section that faces towards a proximal end section of the piston if the drug delivery device is in a final assembly configuration. The contact or abutment surface may be substantially planar and may lie in a plane perpendicular to the axial or longitudinal extension of the piston rod. If the adjusting member comprises a cupped receptacle, the distally facing outer surface of the cupped receptacle of the adjusting member may serve as a contact surface.

In a final assembly configuration of the drug delivery device, the contact surface of the adjusting member may already abut with a proximal end section of the piston. Hence, during assembly of the drug delivery device, the adjusting member may be configured such that, upon reaching the final assembly configuration, the contact surface of the adjusting member is in direct contact with a proximal end of the piston. Thus, the drug delivery device may be ready to use when delivered to customers. An initial set-up step for bringing the piston rod assembly and the piston of the cartridge in abutment with each other is no longer required and becomes superfluous. Mutual abutment of the piston and the piston rod may be such that the piston does not yet apply substantial pressure or thrust to the piston in order to prevent unintended dispensing or generation of droplet at the distal tip of a needle assembly when assembled to the cartridge. Generally, in this way, the overall device handling can be simplified.

However, in another and alternative aspect, it is conceivable that the piston rod assembly is configured during assembly of the drug delivery device in such a way that a pre-defined gap or axial distance between the adjusting member and the piston of the cartridge is attained when the device is in its final assembly configuration. Here, the adjusting member may be manipulated during final assembly of the drug delivery device in such a way that the gap matches with a pre-defined gap size. Further, compensation for the gap may be implemented in the drive mechanism of the drug delivery device. Accordingly, the end user may not have to conduct or trigger a set-up step in which the piston rod assembly and the piston of the cartridge are brought into mutual abutment.

In another aspect, a drug delivery device for dispensing a dose or multiple doses of a medicament is provided. The drug delivery device may comprise a first housing component adapted to receive and to house a cartridge that comprises the medicament, wherein the cartridge comprises a piston slidably arranged therein in an axial direction. By way of the piston, the inner volume of the cartridge is sealed in the proximal direction while the cartridge further comprises an outlet, facing in the distal direction and which is to be coupled with a piercing element, such as an injection needle or a cannula in a fluid-transferring way.

The drug delivery device may further comprise a second housing component which is adapted to house a drive mechanism that comprises a piston rod assembly as described above.

The first and second housing components may be further adapted to be interlocked by way of mutually corresponding fastening means, for instance, by way of a snap-in feature or otherwise, e.g., by way of a threaded engagement. During assembly, and in particular, before the first and second housing components are joined together, the piston rod assembly, which is variable in length, may be adapted to modify an axial gap between the piston rod assembly and the piston of a cartridge to a predefined gap size. Depending on the type of drive mechanism, the gap size may equal zero, wherein the piston rod assembly and the cartridge's piston mutually abut upon assembly of the first and second pre-configured housing components.

Alternatively, in another aspect, the gap size between the piston rod assembly and the piston or between the adjusting member and the piston is larger than zero. The distance between the piston and the piston rod assembly may range, perhaps up to 2.0 mm. However, it may be desirable for the distance to be less than 1 mm. In this aspect, compensation of the gap may be implemented into the drive mechanism of the drug delivery device.

In a further aspect, the axial gap size between the piston rod assembly and the piston of the cartridge is modifiable by way of rotating the adjusting member and/or the piston rod relative to each other during assembly of the drug delivery device. In particular, the piston rod may be rotatably locked with respect to the first and/or second housing components while the adjusting member is threadedly engaged with a distal end section of the piston rod. However, it is also conceivable, that both, the adjusting member and the piston rod are rotatably supported in the respective housing components.

In a further aspect, in particular, wherein the axial gap size between the piston rod assembly and the piston is larger than zero, the drug delivery device may further comprise a drive member that is releasably coupled to the piston rod. The drug delivery device may further comprises a resilient member which is arranged to move the drive member in the proximal direction with respect to the second housing component of the dose delivery, such that the piston rod is moved away from the piston by a pre-defined distance from a position of use, i.e., where the piston and the piston rod assembly mutually abut, into an idle position, in which a pre-defined gap between the piston rod assembly and the piston of the cartridge is attained.

A user may administer a number of pre-set doses of the medicament. For example, when, after dose delivery, a force in the distal direction exerted on the drive member for dose delivery has been removed from the drive member, the drive member is moved in the proximal direction with respect to the housing due to the resilient member interacting with the drive member. The drive member may move in the axial direction with respect to the housing and/or rotate with respect to the housing. The proximal movement of the drive member may take place before the next dose is set. The piston rod may follow at least partly this movement of the drive member in the proximal direction. In particular, the drive member may be moved directly by the resilient member in the proximal direction with respect to the housing, whereas the piston rod may be moved indirectly by the resilient member via the movement of the drive member in the proximal direction with respect to the housing that is transferred to the piston rod. Thus, the piston rod may be moved relative to the piston in the proximal direction. Thereby, the distance between the piston rod and the piston may be increased. In this way, room is provided that allows a deformed piston, in particular an elastically deformed piston, to relax in the proximal direction after dose delivery.

Accordingly, after the piston rod has been moved proximally, the pressure exerted by the piston rod on the piston may be reduced or removed from the piston. Thus, the deformed piston may relax in the proximal direction after dose delivery. Uncontrolled relaxation of the piston in the distal direction, which may result in unintentionally dispensing fluid from the cartridge, may thus be reduced. Furthermore, an increased distance between the piston rod and the piston before setting a subsequent dose may result in reducing the risk of a medicament being unintentionally dispensed from the cartridge, due to vibrations, e.g., as the connection between piston and piston rod is interrupted.

Overall, the dose accuracy may be improved by moving the piston rod in the proximal direction after dose delivery. The piston rod may be moved in the proximal direction after dose delivery only as far as is required for allowing relaxation of the piston in the proximal direction.

The piston rod may be moved in the proximal direction to a well-defined idle position, wherein the distance between the idle position and a position of use, i.e., where the piston rod assembly abuts with the piston of the cartridge, is entirely controlled and adjusted by the drive mechanism. Once the relative position between the piston rod and the adjusting member has been adjusted for the purpose of tolerance elimination, the piston rod assembly can be axially displaced and may even be separated from the piston without introducing any supplemental tolerances.

In another aspect, the drug delivery device may be designed as a disposable device. Hence, during assembly, the first housing component may be equipped with the cartridge filled with the medicament. In the final assembly of the drug delivery device, first and second housing components may be interconnected in a permanent way, such that after consumption of the medicament the entire drug delivery device is intended to be discarded. Accordingly, when the drug delivery device enters the sales market it is already provided with a medicament-filled cartridge and it is ready to use.

In another aspect, a method of assembling a drug delivery device is provided, wherein in a first step a cartridge filled with medicament is positioned in a first housing component to form a cartridge sub-assembly. Also, in a similar way, a drive mechanism that comprises a piston rod assembly is positioned in a second housing component to form a housing sub-assembly. The components of the drug delivery device, such as the piston rod assembly, may take on any features of the above-described aspects.

Thereafter, axial position of the piston may be individually determined with respect to the first housing component, and in a corresponding way, also the axial position of the piston rod assembly may be determined or measured. In particular, the position of the distal end face of the piston rod assembly and/or the position of the proximal end face of the piston may be determined with respect to the first and second housing components, respectively. Having determined or measured axial positions of the piston and the piston rod assembly with respect to their respective sub-assembly or housing component, the axial dimensions or axial elongation of the piston rod assembly may be modified by moving the adjusting member relative to the piston rod, such that the axial distance between the piston and the piston rod assembly equals the pre-defined gap size when the drug delivery device is finally assembled, e.g., by interconnecting cartridge sub-assembly and housing sub-assembly. After having modified the relative axial position of adjusting member and piston rod, the first and second housing components may be mutually interconnected in a final step of assembly.

Axial positions of the piston and/or piston rod assembly may be determined with respect to selected reference points of a respective cartridge or housing sub-assembly or with respect to reference points of respective first and/or second housing components. For instance, mutually corresponding connecting or fastening means of first and second housing components may serve as reference points for determining respective axial positions of the cartridge's piston and/or of the distal end face of the piston rod assembly. Measuring of the relative or absolute positions of the piston and the piston rod and/or of its adjusting member may be conducted in a tactile and/or contactless way, e.g., in an all-optical way.

In a further aspect, the axial position of the piston rod assembly and in particular the axial position of the adjusting member may be modified when the piston rod or the piston rod assembly is in its position of use. Additionally, also determination or measuring of the axial position of the piston rod may be conducted with the piston rod, in particular the piston rod assembly, being in its position of use. This way, any axial tolerances that might be due to the functionality of the drive mechanism to displace the piston rod between a position of use and an idle position are of no consequences and do not have to be considered.

The term "medicament", as used herein, means a pharmaceutical formulation containing at least one pharmaceutically active compound,
wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compounds,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)-4-des Pro36, des Pro37 Exendin-4(1-39)-NH2,
H-(Lys)-5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative; or
an Exendin-4 derivative of the sequence
H-(Lys)6-des Pro36 [Asp28] Exendin-4(1-39)-Lys6-NH2,
des Asp28 Pro36, Pro37, Pro38 Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4 (1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2; or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that changes and modifications may be made to various aspects that have been described above, and that various aspects or their respective features may be combined without departing from the spirit and scope of the claims.

BRIEF DESCRIPTION OF THE DRAWINGS

Without limitation, various exemplary embodiments are described herein with reference to the following drawings, in which.

DETAILED DESCRIPTION

Figure 1:
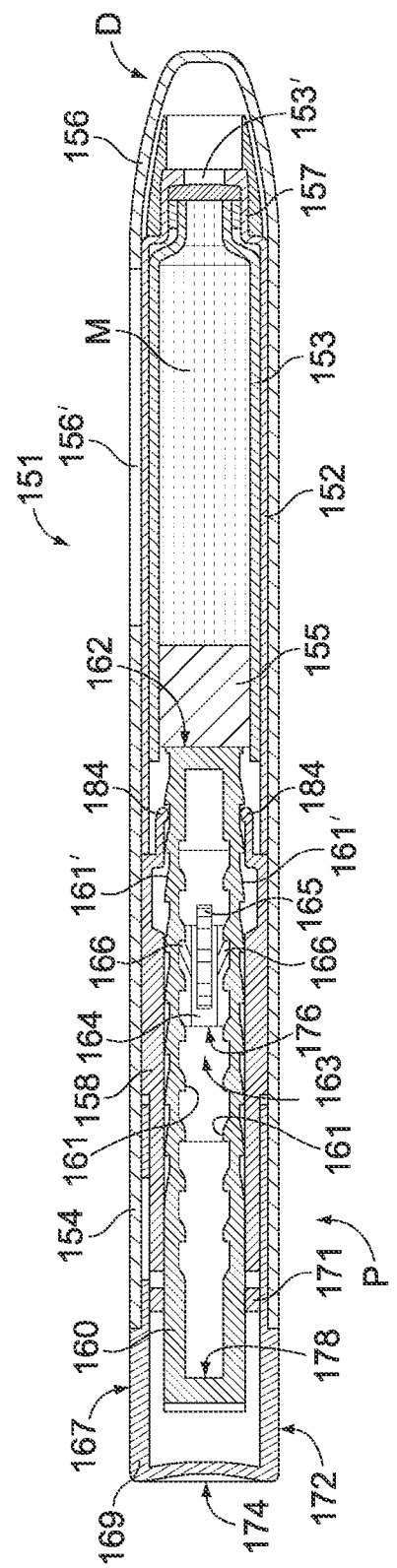
FIG. 1 shows a cross-sectional view of an exemplary embodiment of a drug delivery device in a first, cartridge full, position.

In the embodiment illustrated in FIG. 1, the drug delivery device 151 comprises a cartridge housing 152 and a cartridge 153. The cartridge 153 is retained within the cartridge housing 152. The cartridge has an outlet 153'. The device 151 comprises a main (exterior) housing 154 having a proximal end P and a distal end, which is closest to the dispensing end D of the medication delivery device 1. The proximal end of the cartridge housing 152 and the distal end of the main housing 154 are secured together by any suitable means known to a person skilled in the art. In the illustrated embodiment, the cartridge housing 152 is secured within the distal end of the main housing 154.

The cartridge 153 from which a number of doses of a medicament M may be dispensed is provided in the cartridge housing 152. A piston 155 is retained in the proximal end of the cartridge 153. A removable cap 156 is releasably retained over the distal end of the cartridge housing 152. The removable cap 156 may be optionally provided with one or more windows to the cartridge 156' through which the position of the piston 155 within the cartridge 153 can be viewed.

In the illustrated embodiment, the distal end of the cartridge housing 152 is provided with a distal threaded region 157 designed for the attachment of a suitable needle assembly to enable medication to be dispensed from the cartridge 153. The main housing part 154 is provided with an insert, i.e., internal housing 158. The internal housing 158 is secured against rotational and axial movement with respect to the main housing 154. Alternatively, the internal housing 158 may be formed integrally with the main housing 154. Additionally, the internal housing 158 is provided with a plurality of guide lugs (not shown) and pawl means 184. The pawl means 184 may be an integrated part of the internal housing 158 or may be a separate component.

A piston rod 160 extending through the main housing 154 has a first set of indentations 161' extending longitudinally along external surfaces of the piston rod 160. In particular, the piston rod 160 is designed and arranged to be secured against rotational movement with respect to the main housing 154. A second set of indentations 161 extends longitudinally along internal surfaces of the piston rod 160. The first set of indentations 161' of the piston rod 160 extends through and is engaged with the pawl means 184 provided on the internal housing 158 to prevent movement of the piston rod 160 in the proximal direction with respect to the housing during setting of the dose. A bearing surface 162 located at the distal end of the piston rod 160 is disposed to abut a proximal face of the piston 155. In the illustrated embodiment the longitudinal spacing of the first set of indentations 161' and the second set of indentations 161 is essentially equal, however, in other embodiments the longitudinal spacing of the first set of indentations 161' and the second set of indentations 161 may vary.

A pinion gear 163, consisting of a carrier 164 and a pinion 165, free to rotate within the carrier 164, is located within a channel within the piston rod 160. Pawl arms 166 located on the carrier 164 are releasably engaged with the second set of indentations 161 of the piston rod 160. The pawl arms 166 of the carrier 164 are designed to transmit force to the piston rod 160 in the distal direction during dispensing and to allow relative movement between the pinion gear 163 and the piston rod 160 in the proximal direction during setting the dose. The teeth of the pinion 165 may be permanently engaged with teeth of a second rack (not shown) of the internal housing 158.

A drive member 167 extends about the piston rod 160 and is releasably coupled to the piston rod 160. The drive member 167 comprises a rack part (not shown) and an activation part 169. The rack part and the activation part 169 may be secured to each other in such a way as to prevent rotational and axial movement there between. Alternatively, the drive member 167 may be a unitary component consisting of an integrated rack part and activation part 169.

The rack part is provided with a first rack extending along the main axis of the rack part. The teeth of the first rack of the rack part are permanently engaged with the teeth of the pinion 165.

The drive member 167 has a plurality of guide slots (not shown) in which the guide lugs of the internal housing 158 are located. These guide slots define the extent of permissible axial movement of the drive member 167 with respect to the housing 154. The guide slots may also prevent rotational movement of the drive member 167 relative to the main housing 154.

The drug delivery device 151 further comprises a resilient member 171. The resilient member 171 is arranged to move the drive member 167, and perhaps to move the drive member 167 and the piston rod 160 together, in the proximal direction with respect to the main housing 154 after dose delivery, thereby reducing or even removing pressure of the piston rod 160 on the piston 155. The resilient member 171 is arranged to mechanically interact with the drive member 167 at a distal end side of the drive member 167. The resilient member 171 may be formed integrally with the internal housing 158. Alternatively, the resilient member 171 may be formed integrally with the main housing 154. In another embodiment, the resilient member may be an element separate from the housing and from the internal housing. For instance, the resilient member 171 may be a spring, e.g., a circular spring, a leaf spring or a coil spring.

The activation part 169 of the drive member 167 has a plurality of grip surfaces 172 and a dispensing face 174. To increase intuitiveness of the operation of the medication delivery device 151 and to indicate visual feedback regarding dose setting, the main housing 154 may optionally be provided with a window to the drive member through which graphical status indicators provided on the drive member 167 can be viewed.

In the following, the operation of the drug delivery device 151 will be described.

To set a dose a user grips the grip surfaces 172 of the drive member 167. The user then pulls the drive member 167 in a proximal direction away from the main housing 154 thereby moving the rack part in a proximal direction. The proximal movement of the rack part causes the pinion 165 to rotate and move proximally by virtue of the engagement of the teeth of the pinion 165 of the pinion gear 163 with the teeth of the first rack of the rack part and the teeth of the second rack of the internal housing 158 thus moving the pinion gear 163 in the proximal direction.

The piston rod 160 is prevented from moving proximally by interaction of pawl means 184 of the internal housing 158 with the first set of indentations 161' on the piston rod 160 during dose setting. As the drive member 167 travels in the proximal direction relative to the piston rod 160, the pawl arms 166 of the carrier 164 are elastically displaced inwardly by interaction with the second set of indentations 161 of the piston rod 160.

The proximal travel of the drive member 167 is limited by the guide slots of the drive member 167. At the end of the travel of the drive member 167, the pawl arms 166 of the carrier 164 engage with the next sequential indentation of the second set of indentations 161 of the piston rod 160. The action of the pawl arms 166 of the carrier 164 positively engaging the second set of indentations 161 of the piston rod 160 creates an audible and tactile feedback to the user to indicate that the dose has been set.

When the dose has been set, the user may then dispense this dose by depressing the dispensing face 174 of the activation part 169 of the drive member 167. By this action the drive member 167 and the rack part are moved axially in the distal direction relative to the main housing 154. As the teeth of the pinion 165 of the pinion gear 163 are engaged with the teeth of the first rack of the rack part and the teeth of the second rack of the internal housing 158, the pinion 165 of the pinion gear 163 is caused to rotate and move in the distal direction thus moving the pinion gear 163 longitudinally in the distal direction. As the pawl arms 166 of the carrier 164 of the pinion gear 163 are engaged with the second set of indentations 161 of the piston rod 160, the piston rod 160 is caused to move longitudinally in the distal direction with respect to the internal housing 158.

The distal axial movement of the piston rod 160 causes the bearing surface 162 of the piston rod 160 to bear against the piston 155 in the cartridge 153 causing the piston 155 to be deformed and moved distally, thereby causing a dose of medicament to be dispensed through the attached needle (not shown).

The distal travel of the drive member 167 is limited by the guide slots (not shown) of the drive member 167. Audible and tactile feedback to indicate that the dose has been dispensed is provided by the interaction of the pawl means 184 of the internal housing 158 with the first set of indentations 161' of the piston rod 160. Additionally, visual feedback regarding dose dispense may optionally be indicated by a graphical status indicator, provided on the drive member 167, which can be viewed through the optional window to the drive member in the main housing 154.

When the drug delivery device 151 is in a condition where the maximum number of doses has been delivered, a proximal face 176 of the carrier 164 abuts an internal distal face 178 of the piston rod 160 to prevent further axial movement of the pinion gear 163 and thus the drive member 167 in the proximal direction.

Further doses may be delivered as required up to a predetermined maximum number of doses. After distal movement of the drive member 167 for dose delivery is finished, the resilient member 171 has been biased. For example, a distal end face of the drive member may have moved into abutment with the resilient member 171 and the drive member 167 may have been moved further into the distal direction together with the resilient member 171, thereby biasing the resilient member 171. After the user removes the force acting on the drive member 167 in the distal direction, the biased resilient member 171 moves the drive member 167 and the piston rod 160 in the proximal direction with respect to the main housing 154. Thereby, pressure of the piston rod 160 on the piston 155 is reduced as the piston rod is retracted from the piston. In this way, room for relaxation of the piston in the proximal direction may be provided. Relaxation of the piston 155 in the distal direction may be reduced or avoided in this way. Correspondingly, unintentional weeping of the device may be reduced.

The piston rod 160 and/or the drive member 167 may be moved away from the piston 155 by a distance in the range of about 0.1 to 2.0 mm, in particular in the range of about 0.1 to 0.5 mm, in the proximal direction with respect to the main housing 154 by means of the resilient member 171 moving the drive member 167 in the proximal direction after dose delivery. The distance the drive member 167 is moved does not have to be the same as the distance the piston rod 160 is moved, e.g. the piston rod 160 and the drive member 167 may be coupled with mechanical advantage.

The drug delivery device and its drive mechanism as illustrated and described in FIG. 1 are only exemplary of a variety of drug delivery devices and drive mechanisms that can use one of the exemplary piston rod assemblies as disclosed herein.

Figure 2:
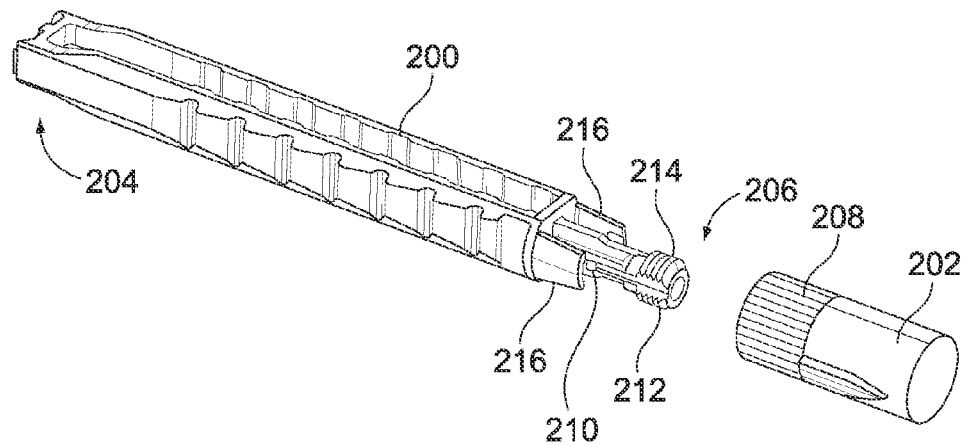
FIG. 2 shows a perspective and isolated illustration of a piston rod assembly with an adjusting member disassembled from the piston rod.
Figure 3:
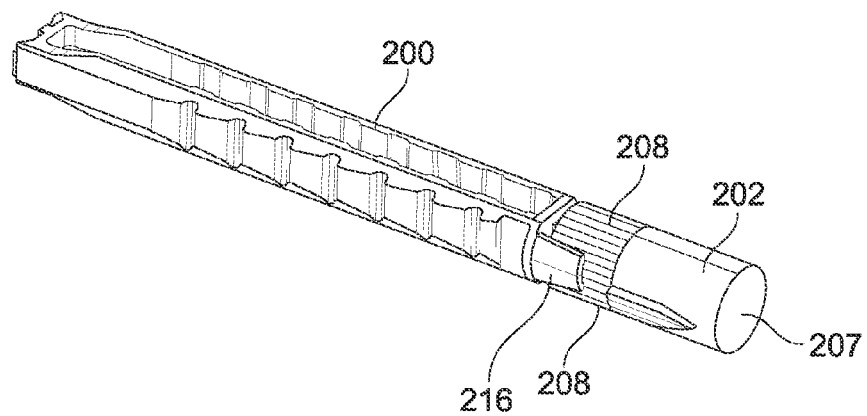
FIG. 3 shows the piston rod assembly according to FIG. 2, wherein the adjusting member and the piston rod are mutually assembled.

FIGS. 2-5 illustrate one embodiment of a piston rod assembly in which the length of the piston rod assembly may be adjusted. As illustrated, the piston rod assembly comprises a piston rod 200 and an adjusting member 202. The embodiment of the piston rod 200 as best illustrated in FIGS. 2 and 3 differs slightly from the piston rod 160 as illustrated in FIG. 1. However, it should be understood that piston rod 200 may be used in place of piston rod 160 in connection with the drug delivery device 151 illustrated in FIG. 1.

As best illustrated in FIG. 2, the piston rod 200 comprises a socket portion 210 at its distal end section. The socket portion 210 is designed as a centrally located and distally extending stud having a threaded head 212 at its free end pointing towards the distal direction. The distally located head 212 comprises an outer thread 214. The proximal end section 204 of the piston rod 200 is configured to be operably engaged with a drive mechanism, such as the exemplary drive mechanism illustrated in FIG. 1.

The adjusting member 202 is designed as a cupped receptacle. It is of substantially hollow cylindrical shape and comprises a receptacle having an opening facing towards the proximal direction. Hence, the adjusting member 202 is adapted to threadedly receive the head 212 of the piston rod's socket portion 210.

Figure 4:
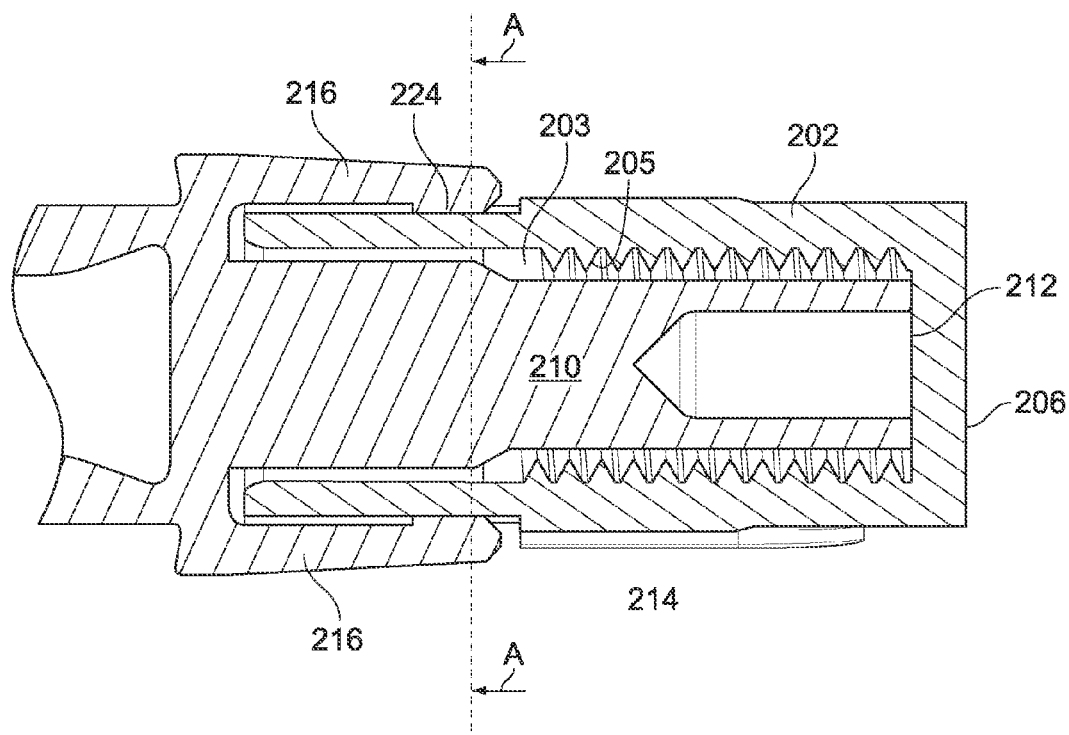
FIG. 4 shows a longitudinal cross-section of the piston rod according to FIG. 3.

As further illustrated in FIG. 4, the receptacle 203 of the adjusting member 202 comprises an inner thread 205 corresponding and matching with the outer thread 214 of the head 212 of the socket portion 210 of the piston rod 200. At its distal end face directed towards a piston of the cartridge, the adjusting member 202 comprises a contact surface 207, which is substantially planar. By way of the contact surface 207, the adjusting member may abut against a proximal end face of the piston 155, perhaps across its entire cross section or surface 207.

By way of the threaded engagement of adjusting member 202 and piston rod 200, the overall axial length of the piston rod assembly can be continuously modified in order to reduce or even to eliminate inevitable production and/or assembly tolerances of the drug delivery device 151.

In order to inhibit self-acting relative rotation of adjusting member 202 relative to the piston rod 200, the piston rod 200 further comprises axially extending tongue members 216 comprising radially inwardly protruding lug portions 224 at least at their distal end section. Since the tongue members 216 are arranged laterally offset from the centrally located socket portion 210, a circumferential gap is formed between said tongue members 216 and the socket portion 210. The size of this circumferential gap is sufficient to receive the cylindrical side wall of the adjusting member 202 as best illustrated in FIG. 4.

Figure 5:
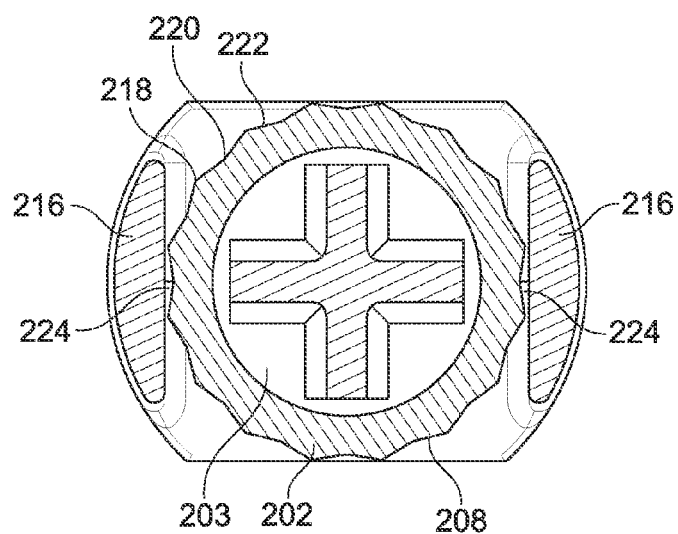
FIG. 5 shows a cross section along A-A according to FIG. 4.

With reference to FIG. 5, In order to provide a kind of snap-in functionality, the adjusting member 202 comprises a corrugated outer surface 208 at its proximal end section. However, in other embodiments, the entire outer surface of the adjusting member may be corrugated. As shown, the corrugations or elongated ribs extend in longitudinal or axial direction. The corrugations may comprise ridge sections 218 and bottom sections 220 regularly and periodically arranged along the outer circumference of the side wall of the adjusting member 202. However, in other embodiments the ridge sections 218 and bottom sections 220 need not be regularly and periodically arranged. Between elevated ridge sections 218 and recessed bottom sections 220, a substantially straight flank or side section 222 extends.

As shown, the profiles of the radially inwardly extending lug portions 224 of the tongue members 216 match the profiles of the corrugated surface 208 of the adjusting member 202. However, a perfect match is not required. Since the tongue members 216 are resiliently biased with respect to the piston rod 200, they can be elastically bent radially outwardly and thus allow the adjusting member 202 to rotate with respect to the piston rod 200.

However, once a pre-defined axial position of the adjusting member has been reached, the positive and/or frictional engagement of the tongue members 216 and the corrugated surface 208 of the adjusting member 202 prevents and inhibits any further self-acting rotation of the adjusting member 202 relative to the piston rod 200. This way, mutual engagement of tongue members 216 and adjusting member 200 provides a self-locking or self-inhibiting threaded engagement of piston rod 200 and adjusting member 202.

Various embodiments have been described above. Those skilled in the art will understand, however, that changes and modifications may be made to those exemplary embodiments, and that different embodiments or their respective features may be combined without departing from the scope of the claims.

List of Reference Numerals
151 drug delivery device
152 cartridge housing
153 cartridge
153' outlet (of cartridge)
154 housing
155 piston
156 removable cap
156' window to cartridge
157 threaded region
158 internal housing (insert)
160 piston rod
161 second indentations (of piston rod)
161' first indentations (of piston rod)
162 bearing surface
163 pinion gear
164 carrier
165 pinion
166 pawl arms
167 drive member
169 activation part
171 resilient member
172 grip surface
174 dispensing face
176 proximal face of carrier
178 distal face of piston rod
184 pawl means
200 piston rod
202 adjusting member
203 receptacle
204 proximal end
205 inner thread
206 distal end
207 contact surface
208 corrugated surface
210 socket portion
212 head portion
214 outer thread
216 tongue member
218 ridge section
220 bottom section
222 side section
224 lug portion
D dispensing end
M medicament
P proximal end

We claim:

1. A piston rod assembly for a drug delivery device, wherein the piston rod assembly is configured to engage a piston of a medicament cartridge, comprising:
   a piston rod having a longitudinal axis and terminating at a distal end;
   an adjusting member displaceably engaged with a distal end of the piston rod, wherein the adjusting member is displaceable along the longitudinal axis of the piston rod while engaged on the distal end, and
   at least one interlock member configured to mutually lock the adjusting member and the piston rod together in an arbitrary relative axial position,
   wherein the interlock member is integral to the piston rod and comprises at least one resiliently biased tongue member, where the resiliently biased tongue member is configured to engage with a portion of a corrugated section of an outer surface of the adjusting member.

2. The piston rod assembly according to claim 1, wherein the interlock member is further configured to at least partially inhibit relative rotation between the piston rod and the adjusting member.

3. The piston rod assembly according to claim 1, wherein the distal end of the piston rod comprises a threaded receptacle configured to receive a threaded socket portion of the adjusting member.

4. The piston rod assembly according to claim 1, wherein the adjusting member comprises a threaded receptacle configured to receive a threaded distal socket portion on the distal end of the piston rod.

5. The piston rod assembly according to claim 4, wherein the adjusting member is displaceably engaged with the distal end section of the piston rod through the threaded receptacle and the threaded distal socket.

6. The piston rod assembly according to claim 1, wherein the resiliently biased tongue member is arranged radially offset with respect to the threaded distal socket portion of the piston rod.

7. The piston rod assembly according to claim 1, wherein the resiliently biased tongue member comprises at least one radially inward projecting lug member.

8. The piston rod assembly according to claim 1, wherein the interlock member comprises two resiliently biased tongue members.

9. A drug delivery device for dispensing medicament, comprising:
   a first housing component configured to house a medicament cartridge;
   a medicament cartridge housed in the first housing component, wherein the medicament cartridge comprises an axially moveable piston;
   a second housing component interlocked with the first housing component, wherein the second housing component is configured to house a drive mechanism; and
   a drive mechanism housed in the second housing component, wherein the drive mechanism comprises a piston rod assembly configured to engage the piston of the medicament cartridge, and wherein the piston rod assembly comprises
   (i) a piston rod having a longitudinal axis and terminating at a distal end,
   (ii) an adjusting member displaceably engaged on the distal end of the piston rod, wherein the adjusting member is displaceable along the longitudinal axis of the piston rod while engaged on the distal end, and
   (iii) at least one interlock member configured to mutually lock the adjusting member and the piston rod together in an arbitrary relative axial position,
   wherein the interlock member is integral to the piston rod and comprises at least one resiliently biased tongue member, where the resiliently biased tongue member is configured to engage with a portion of a corrugated section of an outer surface of the adjusting member.

10. The drug delivery device according to claim 9, wherein the adjusting member comprises a threaded receptacle configured to receive a threaded distal socket portion of the piston rod and the adjusting member is displaceably engaged with the distal end section of the piston rod.

11. The drug delivery device of claim 9, wherein the adjusting member is positioned relative to the piston rod such that a predefined axial distance between a distal end of the piston rod assembly and a proximal end of the piston is attained.

12. The drug delivery device of claim 9, wherein the drive mechanism further comprises a drive member attached to the piston rod assembly such that a force applied to the drive member is at least partially transferred to the piston rod assembly.

13. The drug delivery device of claim 12 further comprising a resilient member arranged in the first housing and configured to exert a proximally directed force on the drive member in response to receiving a distally directed force from the drive member.

14. The drug delivery device of claim 13 wherein the resilient member forces the drive member in a proximal direction with respect to the second housing component after dose delivery such that the piston rod assembly is moved away from the piston a predefined distance.

15. A method of assembling a drug delivery device, comprising:
- positioning a medicament cartridge in a first housing component, wherein the medicament cartridge comprises an axially moveable piston having a proximal end;
- positioning a drive mechanism in a second housing component, wherein the drive mechanism comprises a piston rod assembly having a distal end configured to engage the proximal end of the piston of the medicament cartridge, where the piston rod assembly comprises a piston rod having a distal end and an adjusting member, where the adjusting member is engaged and longitudinally displaceable on the distal end of the piston rod;
- determining an axial position of the piston with respect to the first housing component;
- determining an axial position of the piston rod assembly with respect to the second housing component;
- adjusting the axial position of the piston rod assembly by displacing the adjusting member relative to the piston rod to an axial distance between the distal end of the piston rod assembly and the proximal end of the piston;
- engaging a resiliently biased tongue member of the piston rod assembly with a portion of a corrugated section of an outer surface of the adjusting member;
- interconnecting the first housing component and the second housing component.

16. The method according to claim 15, wherein adjusting the axial position of the piston rod assembly is performed while biasing the piston rod assembly in a distal direction to attain a position of use.

17. The method of claim 15 wherein after adjusting the axial position of the piston rod assembly the adjusting member is locked from further axial moment by at least one interlock member.

* * * * *